(12) United States Patent
Kim et al.

(10) Patent No.: US 7,008,450 B2
(45) Date of Patent: Mar. 7, 2006

(54) POROUS HYDROXY APATITE CONTAINING SILICON AND MAGNESIUM, AND A PREPARATION METHOD THEREOF

(75) Inventors: Soo-Ryong Kim, Seoul (KR); Young Hee Kim, Seoul (KR); Yoon Joo Lee, Seoul (KR); Hae-Jung Kim, Chungcheongbuk-Do (KR); Sang-Jin Jung, Seoul (KR); Hee Song, Seoul (KR)

(73) Assignees: Korea Institute of Ceramic Engineering and Technology, Seoul (KR); Meta Biomed Co., Ltd., Chuncheongbuk-Do (KR)

(*) Notice: Subject to any disclaimer, the term of this patent is extended or adjusted under 35 U.S.C. 154(b) by 105 days.

(21) Appl. No.: 10/647,450

(22) Filed: Aug. 26, 2003

(65) Prior Publication Data

US 2004/0078087 A1    Apr. 22, 2004

(30) Foreign Application Priority Data

Aug. 30, 2002   (KR) ...................... 10-2002-0052044

(51) Int. Cl.
*A61F 2/02* (2006.01)
*C01B 25/32* (2006.01)
*C04B 12/02* (2006.01)

(52) U.S. Cl. .............. 623/11.11; 623/16.11; 623/23.61; 423/308; 106/462

(58) Field of Classification Search ............ 623/16.11, 623/23.51, 23.56, 23.61, 919; 423/308–311; 106/462

See application file for complete search history.

(56) References Cited

U.S. PATENT DOCUMENTS

| | | | |
|---|---|---|---|
| 3,890,107 A | 6/1975 | White et al. | |
| 3,929,971 A | 12/1975 | Roy | |
| 4,861,733 A | 8/1989 | White | |
| 4,976,736 A | 12/1990 | White et al. | |
| 6,024,985 A | 2/2000 | Simkiss et al. | |
| 6,312,468 B1 | 11/2001 | Best et al. | |

FOREIGN PATENT DOCUMENTS

| | | |
|---|---|---|
| EP | 0278583 | 2/1988 |
| WO | WO 98/08773 | 3/1998 |

OTHER PUBLICATIONS

Science, Jan. 16, 1970, vol. 167, pp. 279-280.
Bioceramics, vol. 7, Edited by O.H. Andersson and A. Yli-Urpo, 1994 Butterworth-Heinemann Ltd., pp. 49-54.
Biomaterials, 1996, vol. 17, No. 17, pp. 1709-1714.
Materials Characterization 47, 2001, pp. 83-87.
Materials Science & Engineering C6, 1998, pp. 175-182.
Journal of Materials Synthesis and Processing, vol. 8, Nos. 5/6, 2000, pp. 305-311.
Biomaterials, 1995, vol. 16, No. 9, pp. 703-707.
Journal of Inorganic Biochemistry, 66, 1997, pp. 1-6.
J. Aust. Ceram. Soc., 29 [1/2], 1993, pp. 71-80.
Key Engineering Materials, vols. 192-195, 2001, pp. 247-250.
Journal of Materials Science, 28, 1993, pp. 9-14.
J. Biomed. Mater. Res., 44, 1999, pp. 422-428.

*Primary Examiner*—David J. Isabella
(74) *Attorney, Agent, or Firm*—Morrison & Foerster LLP

(57) ABSTRACT

Disclosed are a silicon- and magnesium-containing porous hydroxyapatite, and a preparation method thereof which comprises the steps of performing a hydrothermal treatment of a natural coral and performing a solvothermal treatment.

7 Claims, 4 Drawing Sheets

POROUS HYDROXY APATITE CONTAINING SILICON AND MAGNESIUM, AND A PREPARATION METHOD THEREOF

BACKGROUND OF THE INVENTION

1. Field of the Invention

The present invention relates to a porous hydroxyapatite which can be used as a biomaterial, and to a preparation method thereof.

2. Description of the Background Art

It has been known that an apatite exhibits an excellent bioactivity and bone conduction, and thus, has been widely used as a bio-ceramic. It is advantages since it is similar to bones in composition compared to other bio-ceramics such as a bioglass or A-W glass.

Bioactive ceramics that have been used as bone replacement materials, i.e., CaO, $SiO_2$, MgO-based glass ceramics, contain significant amount of silicon and magnesium ions. Kokubo et al. has presented a theory that silicon existing in the glass ceramics is gradually released in a simulated body fluid to become a silicate ion present on a surface of the glass ceramics, and such silicate ion makes a new apatite nucleus be formed, and therefore, an apatite layer is formed quickly on the surface of the glass ceramics (Bioceramics vol. 7, 49, 1994). Carlisle et al. has discovered through an electron microprobe research that silicon plays a critical role for generation of bones. That is, chemical analysis results showed that newly formed bones always contain about 0.5% of silicon (Science, vol 167, 279, 1970), which supports the Kokubo's theory.

In order the ceramic materials to be used as a substitute material for bone, it should be quickly associated with live bones. For this purpose, a bone substitute material should have porous structure in which pores in size of 300–500 $\mu$m are three-dimensionally connected with each other. This is required because when the bone substitute material is actually implanted into a body, a body fluid can freely pass through the pores so that a new bone can be generated.

A natural coral is similar to a human cancellous bone in structure that it comprises calcium carbonate and has three-dimensionally connected pores in size of 200–500 $\mu$m. A method for converting a natural coral into an apatite by performing a hydrothermal treatment while maintaining its microstructures has been reported (U.S. Pat. Nos. 3,890,107 and 3,929,971; Biomaterials 17(17), p1709, 1996; and Material Characterization 47(2), p83, 2001).

Since a coral-derived natural apatite bone replacement material (Pro Osteon 200, 500, 200R, 500R) has become available from Interpore Co. in 1995 and used in a general surgical operation method, interests in and researches into the porous implant using a synthetic apatite have been accelerated.

There has been known a method for preparing a composite calcium phosphate of hydroxyapatite, tricalcium phosphate, tetracalcium phosphate, etc. from a natural coral showing an increased bioactivity and biodegradation rate, by changing reaction temperature, time, etc. of the hydrothermal process (U.S. Pat. No. 4,861,733 and European Patent Application No. 0,278,583). In addition, a method for converting only surface of the coral into hydroxyapatite (U.S. Pat. No. 4,976,736) has been proposed. In those methods, Ca/P ratios in calcium phosphate have been changed to vary the composition of the calcium phosphate, thereby to render a bioactivity to the hydroxyapatite.

However, in the apatite consisting of actual bones of a body, some of Ca, P and O sites are substituted with a small amount of other ions. In this case, even if a small amount of other ions are substituted, the substituted ions can make a great influence on surface charge, surface structure, strength, solubility, etc. of the apatite. In order to develop materials being similar to actual bones in composition, researches for preparing an apatite containing various ions have been performed.

It has been known that silicon exists as silicate ion, which has a tetrahedral structure, in a hydroxyapatite structure. There has been reported an example that P site of the hydroxyapatite has been substituted with silicon (European Patent Application No. 0,951,441; WO 98/08773; and U.S. Pat. No. 6,312,468). Besides, there has been also reported an example that Ca site of the hydroxyapatite has been substituted with magnesium (U.S. Pat. No. 6,585,946).

The present Inventors have reported a method for preparing hydroxyapatite powder containing silicon and magnesium ions using $Ca(OH)_2$ and $H_3PO_4$ as starting materials and its sintering behavior in Biomaterials, vol 24, 1389, 2003.

In order to be used as a bone replacement material, a porous structure is required to be processed such that have pores in size of 300–500 $\mu$m which are three-dimensionally connected with each other.

In a conventional preparation method of a porous hydroxyapatite, hydroxyapatite slurry is infiltrated into a polyurethane foam and the resultant is then sintered. However, this method is not so much favorable, because volatile organic compounds generated during sintering process make a bad influence on the environment, as well as mechanical strength of the porous hydroxyapatite prepared by this method is very weak, which makes it difficult for the product to be stored, transported and used in surgical operation.

Meanwhile, since a natural coral is made of calcium carbonate and has three-dimensionally connected pores in size of 200–500 $\mu$m, it is similar to human cancellous bones in structure, so that it can be preferably used as a starting material for synthesis of hydroxyapatite. Another advantage is that mechanical strength of the hydroxyapatite prepared from a coral is very high.

It has been known that a comprehensive strength of the porous hydroxyapatite prepared from a natural coral is about 5.8 Mpa (Materials Science and Engineering C6, 175, 1998), which is much higher compared that that of the porous hydroxyapatite prepared by the conventional method as described above is about 1.3 Mpa.

SUMMARY OF THE INVENTION

Therefore, an object of the present invention is to provide a silicon- and magnesium-containing porous hydroxyapatite in which its bioactivity is increased by changing its composition and form, into a level similar to animal bones including a human while maintaining microstructures of a coral, and to a preparation method thereof.

BRIEF DESCRIPTION OF THE DRAWINGS

The accompanying drawings, which are included to provide a further understanding of the invention and are incorporated in and constitute a part of this specification, illustrate embodiments of the invention and together with the description serve to explain the principles of the invention.

In the drawings.

DETAILED DESCRIPTION OF THE PREFERRED EMBODIMENTS

Figure 1:
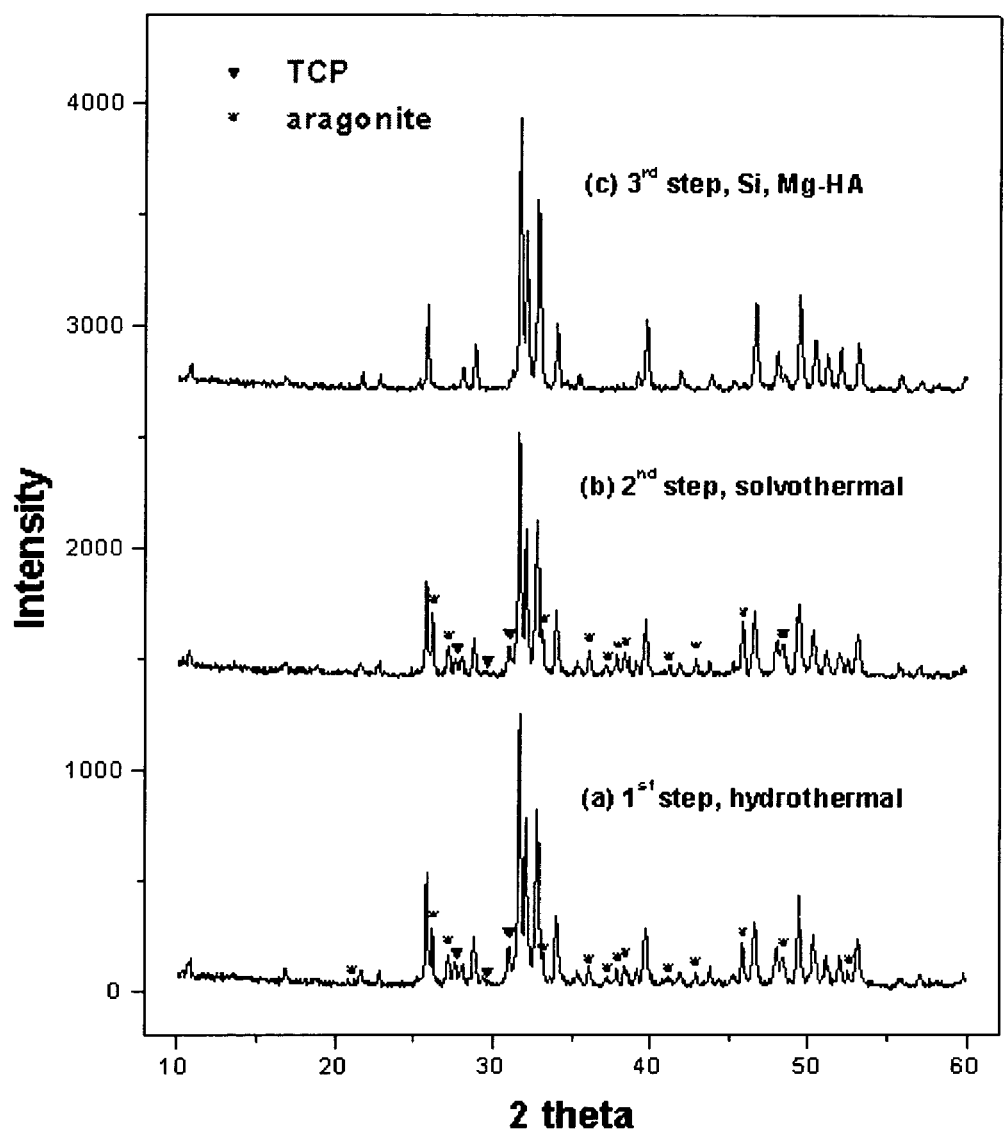
FIG. 1 is a graph showing X-ray diffraction analysis data for the porous hydroxyapatite prepared in Example 2 of the present invention.

The present invention relates to a silicon- and magnesium-containing porous hydroxyapatite, and to a preparation method thereof.

The porous hydroxyapatite of the present invention contains silicon and magnesium ions in an amount of 0.05–5 wt %, respectively, to the total weight of the porous hydroxyapatite, and has pores in size of 200–500 $\mu$m which are three-dimensionally connected with each other. Thus, in composition and structure, it is very similar to human cancellous bone.

Therefore, the silicon- and magnesium-containing porous hydroxyapatite of the present invention has excellent bioactivity so that it can be used as an artificial bone including a spine or long bone, or various body tissues including an orbital implant or chin implant, medical materials, or the like.

A preparation method of the silicon- and magnesium-containing porous hydroxyapatite of the present invention will now be described.

In the present invention, a natural coral may be used as a starting material for preparing the silicon- and magnesium-containing porous hydroxyapatite.

A natural coral comprises $CaCO_3$ in an aragonite crystal phase as a main component. According to chemical analysis, the natural coral always contains magnesium ion in an amount of about 0.098–0.150 wt % depending on a sample. The reason of a natural coral contains magnesium ion is as follows. Among ions of Ca, Mg, K, Na, Fe, etc. which is present in seawater, $Mg^{2+}$ ion is similar to $Ca^{2+}$ ion in ionic radius, and thus, while a coral is growing, $Ca^{2+}$ ion site can be easily substituted with $Mg^{2+}$ ion.

A coral sample used in the present invention is not restricted to specific species, but a porities species of which fine structure is similar to human cancellous bones is preferably used. Preferably, a natural coral is used after being pre-treated with a NaOCl solution in order to remove an organic material existing therein.

The preparation method of the silicon- and magnesium-containing porous hydroxyapatite in accordance with the present invention comprising the following steps of:

(1) performing a hydrothermal reaction of a coral sample pre-treated with a NaOCl solution in an excess amount of an aqueous $(NH_4)_2HPO_4$ solution; and (2) performing a solvothermal treatment of a product obtained in step (1) in a saturated solution of a silicon acetate in acetone, to obtain a porous hydroxyapatite containing silicon and magnesium ions.

In step (1), there is no restriction on the concentration of the aqueous $(NH_4)_2HPO_4$ solution, but 2M solution is preferably used. The hydrothermal reaction is preferably performed at a temperature of 150–300° C. for 6–30 hours in a Teflon-coated hydrothermal bomb made of a stainless steel (e.g. an autoclave), which is put into an oven.

In step (2), the solvothermal treatment is preferably performed at a temperature of 100–250° C. for 12–36 hours.

When the step (2) is completed, a porous hydroxyapatite is obtained of which a part of calcium ion sites and phosprous ion sites of the coral have been substituted with magnesium ions and silicon ions, respectively.

In order to obtain a silicon- and magnesium-containing porous hydroxyapatite in single phase, the hydrothermal reaction in step (1) may be preferably performed repeatedly after step (2) is completed. In this case, reaction conditions may be the same as described above.

EXAMPLES

The present invention will now be described in more detail though Examples and Comparative Examples. Examples are only to illustrate the present invention and not to limit the scope of the invention thereto.

In the following Examples and Comparative Examples, a coral sample of porities species was cut thin and soaked in a 5% sodium hypochlorite solution for 30 hours in order to remove organic materials contained therein.

XRD analysis was performed with a MacScience diffractometer using a Cu Ka radiation, after the sample was washed sequentially with acetone and distilled water in an ultrasonic bath and then dried.

Example 1

A coral sample was put into an excess amount of 2M aqueous $(NH_4)_2HPO_4$ solution and hydrothermally treated at a temperature of 180° C. for 7 hours. A saturated silicon acetate solution in 30 ml of acetone was put into a Teflon-coated stainless steel autoclave. 0.9 g of coral sample obtained from hydrothermal reaction was put into the autoclave, which was then sealed. The autoclave was put into an oven, and solvothermal treatment was performed at 180° C. for 24 hours so as to make silicon ion to be inserted into hydroxyapatite framework.

The products of the hydrothermal-treatment and solvothermal-treatment were respectively washed sequentially with acetone and distilled water in an ultrasonic bath and then dried. XRD analysis was then performed therefor, of which results are shown in FIG. 1. Curve (a) in FIG. 1 shows XRD analysis data for the hydrothermal treated product, while curve (b) in FIG. 1 shows XRD analysis data for the solvothermal-treated product. Curves (a) and (b) in FIG. 1 show that both products of hydrothermal treatment and solvothermal treatment are mixtures of hydroxyapatite, tricalcium phosphate and $CaCO_3$ (aragonite phase).

Next, the solvothermal-treated sample was put into an excess amount of 2M aqueous $(NH_4)_2HPO_4$ solution and then hydrothermally reacted again at a temperature of 180° C. for 24 hours so as to make the sample to be converted into a hydroxyapatite in single phase. The obtained product was washed sequentially with acetone and distilled water in the ultrasonic bath and dried.

The results of XRD analysis confirmed that the final product is hydroxyapatite in single phase (See curve (c) in FIG. 1). An Energy Dispersive Spectroscopy ("EDS") analysis shows that silicon and magnesium ions were detected from every portion of the hydroxyapatite framework, and thus demonstrates that a part of Ca sites and P sites were substituted with magnesium ions and silicon ions in the hydroxyapatite prepared herein. A quantitative analysis with an Inductively Coupled Plasma ("ICP") Spectroscopy shows that silicon and magnesium contents were respectively 0.3 wt % and 0.1 wt %.

Example 2

A coral sample was put into an excess amount of 2M aqueous $(NH_4)_2HPO_4$ solution and then hydrothermally reacted at a temperature of 180° C. for 16 hours. A saturated silicon acetate solution in 30 ml of acetone was put into a Teflon-coated stainless steel autoclave. 0.9 g of coral sample obtained from hydrothermal treatment was put into the autoclave, which was then sealed. The autoclave was put into an oven, and solvothermal treatment was performed at 180° C. for 24 hours so as to make silicon ion to be inserted into hydroxyapatite framework.

The solvothermal-treated sample was put into an excess amount of 2M aqueous $(NH_4)_2HPO_4$ solution and then hydrothermally reacted again at a temperature of 180° C. for 24 hours so as to make the sample to be converted into a hydroxyapatite in single phase. The obtained product was washed sequentially with acetone and distilled water in the ultrasonic bath and dried.

The results of XRD analysis confirmed that the final product is hydroxyapatite in single phase. In an EDS analysis, silicon and magnesium ions were detected from every portion of the hydroxyapatite framework. According to a result a quantitative analysis with an ICP Spectroscopy, silicon and magnesium contents were respectively 0.8 wt % and 0.1 wt % of the total weight of the hydroxyapatite prepared.

Example 3

A coral sample was put into an excess amount of 2M aqueous $(NH_4)_2HPO_4$ solution and hydrothermally treated at a temperature of 180° C. for 16 hours. A saturated silicon acetate solution in 30 ml of acetone was put into a Teflon-coated stainless steel autoclave. 0.9 g of coral sample obtained from hydrothermal treatment was put into the autoclave, which was then sealed. The autoclave was put into an oven, and solvothermal treatment was performed in an oven at 200° C. for 24 hours so as to make silicon ion to be inserted into hydroxyapatite framework.

The solvothermal-treated sample was put into an excess amount of 2M aqueous $(NH_4)_2HPO_4$ solution and then hydrothermally reacted again at a temperature of 200° C. for 24 hours so as to make the sample to be converted into a hydroxyapatite in single phase. The obtained product was washed sequentially with acetone and distilled water in the ultrasonic bath and dried.

The results of XRD analysis confirmed that the final product is hydroxyapatite in single phase. In an EDS analysis, silicon and magnesium ions were detected from every portion of the hydroxyapatite framework. According to a result a quantitative analysis with an ICP Spectroscopy, silicon and magnesium contents were respectively 1.5 wt % and 0.1 wt % of the total weight of the hydroxyapatite prepared.

Comparative Example 1

Pure hydroxyapatite without containing silicon or magnesium was prepared from a coral in the following manner:

A certain amount of coral was cut thin and dipped in a 2M aqueous $(NH_4)_2HPO_4$ solution, and then transferred into a Teflon-coated hydrothermal bomb made of stainless steel. The hydrothermal bomb was put into an oven, and a hydrothermal treatment was carried therein at a temperature of 200° C. for 48 hours.

After reaction was completed, the coral was taken, washed sequentially with acetone and distilled water in the ultrasonic washer and then dried, to obtain a pure hydroxyapatite.

XRD analysis confirmed that the prepared hydroxyapatite as described above is a hydroxyapatite in single phase. In an EDS analysis, only magnesium ion was detected from every portion of the hydroxyapatite framework. The reason why only magnesium ion was detected is apparently because 0.098–0.150 wt % of magnesium ion are always present in a natural coral.

Comparative Example 2

A coral sample of 0.9 g was put in a Teflon-coated hydrothermal bomb made of stainless steel, to which a 30 ml of 2M aqueous $(NH_4)_2HPO_4$ solution and 0.5 g of silicon acetate as a silicon raw material were added. Hydrothermal treatment was then performed at a temperature of 200° C. for 48 hours, to obtain porous hydroxyapatite.

Figure 3:
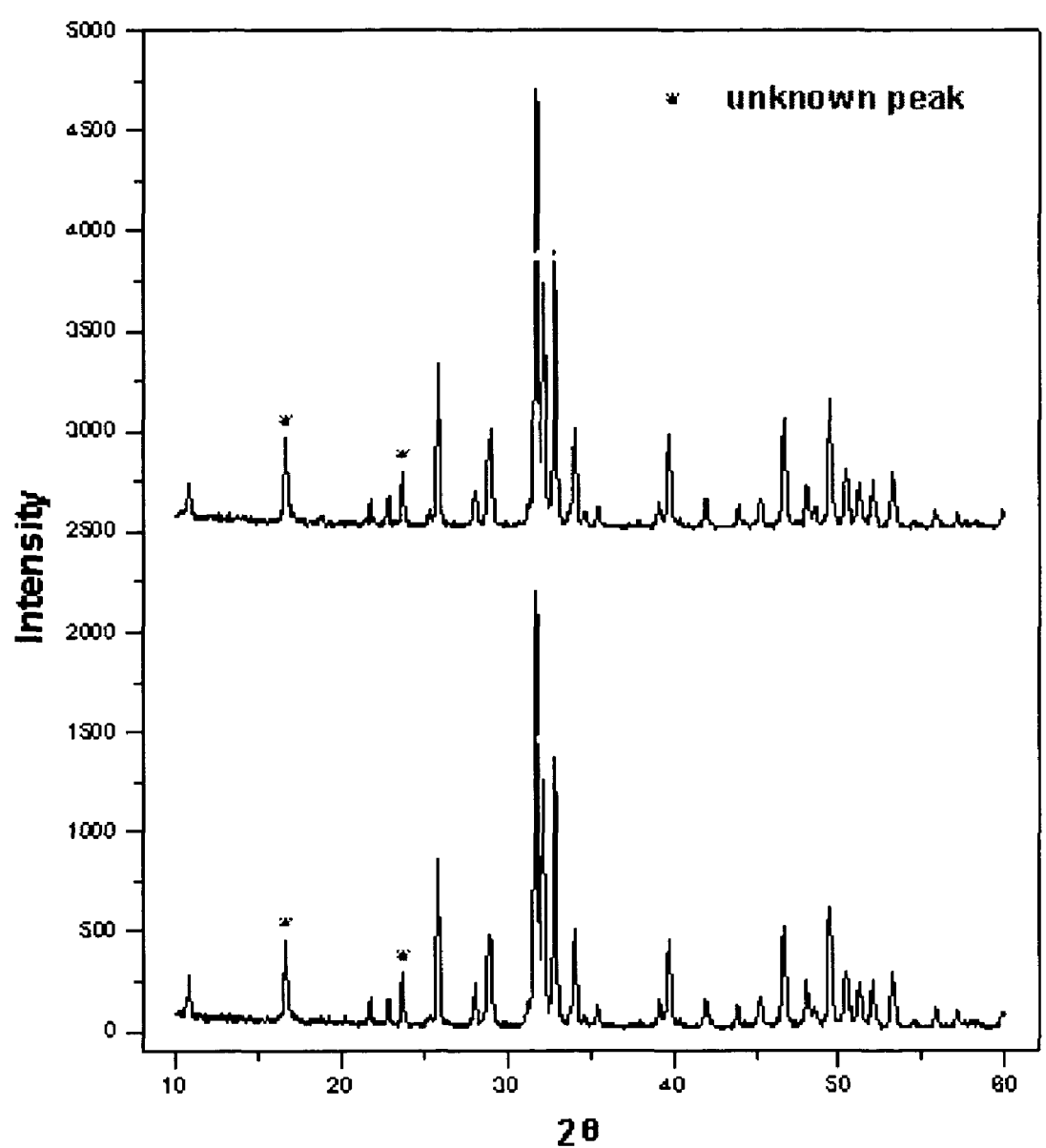
FIG. 3 is a graph showing X-ray diffraction analysis data for the porous hydroxyapatite prepared by a hydrothermal synthesis in Comparative Examples 1 (top) and 2 (bottom).

According to an XRD analysis result on the final product, besides hydroxyapatite peaks, two unknown peaks, which were estimated as ammonium silicate, were observed (See the upper curve in FIG. 3). In an EDS analysis, only magnesium ion was detected from every portion of the hydroxypatite framework, and no silicon ion was detected.

Comparative Example 3

A coral sample of 0.9 g was put into a Teflon-coated hydrothermal bomb made of stainless steel, to which a 30 ml of 2M aqueous $(NH_4)_2HPO_4$ solution and 0.5 g of tetraethylorthosilicate as a silicon raw material were added. Hydrothermal treatment was performed at a temperature of 200° C. for 48 hours, to obtain porous hydroxyapatite.

According to an XRD analysis result on the final product, likewise in the Comparative Example 1, besides hydroxyapatite peaks, two unknown peaks, which were estimated as ammonium silicate, were observed (See the lower curve in FIG. 3). In an EDS analysis, only magnesium ion was detected from every portion of the hydroxypatite framework, and no silicon ion was detected.

Example 4

Bioactivity Test

In order to identify bio-affinities of the silicon- and magnesium-containing porous hydroxyapatite prepared in Example 1 and the pure hydroxyapatite prepared in Comparative Example 1, animal experiments were performed as follows:

The silicon- and magnesium-containing porous hydroxyapatite prepared in Example 1 and the pure hydroxyapatite prepared in Comparative Example 1 were respectively cut into a cylindrical shape with a diameter of 5 mm and a length of 8 mm, sterilized, and then implanted respectively into lateral femoral condyles of two different New Zealand White Rabbits.

The rabbits were sacrificed after 3, 6 and 20 weeks from implantation, the artificial bone-implanted lateral femoral condyles were cut with a diamond saw. The cut portions were fixed in 2.5% glutaraldehyde, and then dehydrated by passing through an ethanol solution. Interactions between the implanted sample and bone tissues around the implanted sample were observed, and the results are shown in FIGS. 2A to 2F.

Figure 2A:
FIGS. 2A to 2F are photographs showing changes of a pure hydroxyapatite porous body and a Si- and Mg-containing porous hydroxyapatite over time after being implanted respectively into a lateral femoral condyle of a New Zealand White Rabbit.
Figure 2B:
Figure 2C:
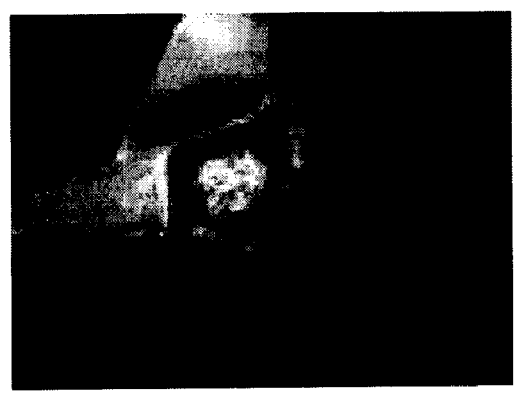
Figure 2D:
Figure 2E:
Figure 2F:
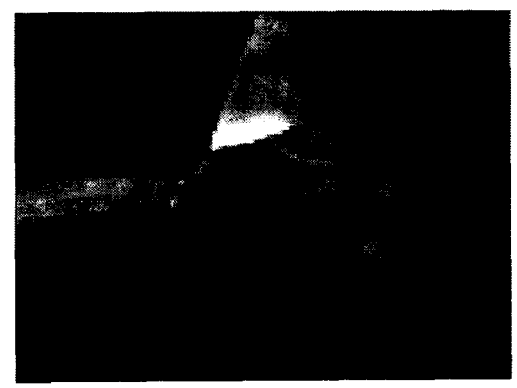

FIGS. 2A, 2B and 2C respectively show results of the pure hydroxyapatite after 3, 6 and 20 weeks from implantation, and FIGS. 2D, 2E and 2F respectively show results of the silicon- and magnesium-containing porous hydroxyapatite after 3, 6 and 20 weeks from implantation.

As can be seen from FIGS. 2A, 2B and 2C, when the pure hydroxyapatite porous body was implanted, it was observed that form of the sample has been maintained as it is even after 20 weeks from implantation.

In the case of the porous hydroxyapatite containing silicon and magnesium ions, it seems that after 6 weeks, though form of the sample has been maintained yet, neighboring bone marrow was filled in the implanted sample (See FIG. 2D). In addition, it can be seen from FIG. 2F that after 20 weeks, the sample site was completely filled with bone marrow.

Therefore, it was discovered that the silicon- and magnesium-containing porous hydroxyapatite according to the present invention is superior to pure hydroxyapatite porous body in bioactivity.

What is claimed is:

1. A silicon- and magnesium-containing porous hydroxyapatite, comprising three-dimensionally connected pores in size of 200–500 μm and having substantially a human cancellous bone structure, and comprising silicon and magnesium ions in an amount of 0.05–5 wt %, respectively.

2. A preparation method of a silicon- and magnesium-containing porous hydroxyapatite, comprising the steps of:

(1) performing a hydrothermal treatment of a coral sample pre-treated with a NaOCl solution in an aqueous $(NH_4)_2 HPO_4$ solution; and (2) performing a solvothermal treatment of the coral sample prepared in step (1) in a saturated solution of silicon acetate in acetone, to obtain the silicon- and magnesium-containing porous hydroxyapatite, wherein the coral sample comprises magnesium ions.

3. The preparation method according to claim 2, wherein contents of silicon and magnesium in the silicon- and magnesium-containing porous hydroxyapatite obtained in step (2) are 0.05–5 wt %, respectively.

4. The preparation method according to claim 2, wherein the step (1) is performed at 150–300° C. for 6–36 hours.

5. The preparation method according to claim 2, wherein the step (2) is performed at 100–250° C. for 12–36 hours.

6. The preparation method according to claim 2, wherein the step (1) is repeatedly performed after completion of the step (2), to obtain a porous hydroxyapatite in single phase.

7. A silicon- and magnesium-containing porous hydroxyapatite used for an artificial bone including a spine or long bone, an orbital implant, or a chin implant, comprising three-dimensionally connected pores in size of 200–500 μm, and having substantially a human cancellous bone structure, and comprising silicon and magnesium ions in an amount of 0.05–5 wt %, respectively.

* * * * *

(12) EX PARTE REEXAMINATION CERTIFICATE (7245th)
United States Patent
Kim et al.

(10) Number: US 7,008,450 C1
(45) Certificate Issued: Dec. 15, 2009

(54) POROUS HYDROXY APATITE CONTAINING SILICON AND MAGNESIUM, AND A PREPARATION METHOD THEREOF

(75) Inventors: Soo-Ryong Kim, Seoul (KR); Young Hee Kim, Seoul (KR); Yoon Joo Lee, Seoul (KR); Hae-Jung Kim, Chungcheongbuk-Do (KR); Sang-Jin Jung, Seoul (KR); Hee Song, Seoul (KR)

(73) Assignees: Korea Institute of Ceramic Engineering and Technology, Geumcheon-Gu, Seoul (KR); Meta Blomed Co., Ltd., Heungdeok-Gu, Cheongju, Chungcheongbuk-Do (KR)

Reexamination Request:
No. 90/009,396, Jan. 29, 2009

Reexamination Certificate for:
Patent No.: 7,008,450
Issued: Mar. 7, 2006
Appl. No.: 10/647,450
Filed: Aug. 26, 2003

(30) Foreign Application Priority Data
Aug. 30, 2002 (KR) .................. 1020020052044

(51) Int. Cl.
*A61F 2/02* (2006.01)
*C01B 25/32* (2006.01)
*C04B 12/02* (2006.01)

(52) U.S. Cl. .............. 623/11.11; 106/462; 423/308; 623/16.11; 623/23.61

(58) Field of Classification Search .................. None
See application file for complete search history.

(56) References Cited

U.S. PATENT DOCUMENTS

| 4,976,736 A | 12/1990 | White et al. |
| 2002/0127260 A1 | 9/2002 | Riman et al. |

FOREIGN PATENT DOCUMENTS

| WO | 1998/08773 | 3/1998 |
| WO | 2001/12106 A1 | 2/2001 |

*Primary Examiner*—Cary E. O'Connor

(57) ABSTRACT

Disclosed are a silicon- and magnesium-containing porous hydroxyapatite, and a preparation method thereof which comprises the steps of performing a hydrothermal treatment of a natural coral and performing a solvothermal treatment.

EX PARTE REEXAMINATION CERTIFICATE ISSUED UNDER 35 U.S.C. 307

THE PATENT IS HEREBY AMENDED AS INDICATED BELOW.

AS A RESULT OF REEXAMINATION, IT HAS BEEN DETERMINED THAT:

Claims 1 and 7 are cancelled.

Claims 2–6 were not reexamined.

\* \* \* \* \*